United States Patent
Trowell et al.

(10) Patent No.: US 7,029,869 B2
(45) Date of Patent: Apr. 18, 2006

(54) FEEDING ASSAY FOR IDENTIFYING NEMATICIDAL COMPOUNDS

(75) Inventors: Stephen Charles Trowell, Oxley (AU); Chunyan Liao, Red Hill (AU); Peter David East, O'Connor (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 31 days.

(21) Appl. No.: 10/148,352

(22) PCT Filed: Nov. 30, 2000

(86) PCT No.: PCT/AU00/01476

§ 371 (c)(1),
(2), (4) Date: Aug. 8, 2002

(87) PCT Pub. No.: WO01/40500

PCT Pub. Date: Jun. 7, 2001

(65) Prior Publication Data

US 2003/0012732 A1    Jan. 16, 2003

(30) Foreign Application Priority Data

Nov. 30, 1999   (AU) .................................. PQ 4367

(51) Int. Cl.
 C12Q 1/02    (2006.01)
 C12N 1/00    (2006.01)
 A61K 49/00   (2006.01)

(52) U.S. Cl. .......................... 435/29; 435/243; 424/9.2

(58) Field of Classification Search ................ 435/968, 435/29, 243; 424/9.2
See application file for complete search history.

(56) References Cited

U.S. PATENT DOCUMENTS

| 5,580,749 | A | * | 12/1996 | Hughes | ........................ 435/29 |
| 6,006,470 | A | * | 12/1999 | Geoghegan et al. | ..... 47/58.1 R |
| 6,540,996 | B1 | * | 4/2003 | Zwaal et al. | .............. 424/93.21 |
| 6,664,441 | B1 | * | 12/2003 | Verwaerde et al. | ............ 800/3 |
| 6,787,125 | B1 | * | 9/2004 | Verwaerde et al. | .......... 424/9.1 |

OTHER PUBLICATIONS

De Coen et al. "The use of biomarkers in *Daphinia magna* testing. III. Rapid toxicity testing of pure chemicals and sediment pore waters using ingestion and digestive enzyme activity" (1998) Chemosphere 37(13): 2677-2694.*

Jones et al. "Feeding in inhibited by sublethal concentrations of toxicants and by heat stress in the nematode *Caenorhabditis elegans*: Relations to the cellular stress response." (Jul. 1, 1999) J. Exp. Zool. 284(2): 147-157.*

Bockenhoff et al. Studies on the nutrient uptake by the beet cyst nematode *Heterodera schachii* by in situ microinjection of fluorescent probes into the feeding structures in *Arabidopsis thaliana*. (1994) Parasitology 109: 249-254.*

Boyd et al. "The effects of metals and food availability on the behavior of *Caenorhabditis elegans*." (2003) Environ. Toxicol. Chem. 22(12): 3049-3055.*

Avery et al. "Effect of starvation and neuroactive drugs on feeding in *Caenorhabditis elegans*." (1990) Exp. Zool. 253:263-270.*

Hecht et al. "Simple adaptations to extend the range of flow cytometry five orders of magnitude fo the DNA analysis of uni- and multicellular systems." (1981) 29(6): 771-774.*

Hawdon et al. "Serum-stimulated feeding in vitro by third-stage infective larvae of the canine hookworm *Ancylostoma caninum*." (1990) J. Parasitol. 76(3): 394-398.*

Moffat et al "Fluorescent lipid uptake and transport in adult *Schistosoma mansoni*." (1992) 105:81-89.*

Yeates, G.W. (1998) "Feeding in free-living soil nematodes: a functional approach." In Perry, R.N., Wright D.J., eds, The Physiology and Biochemistry of Free-living and Plant parasitic nematodes. CAB International: New York, p. 245-269.*

(Continued)

*Primary Examiner*—Jean C. Witz
*Assistant Examiner*—Susan Hanley
(74) *Attorney, Agent, or Firm*—Greenlee Winner and Sullivan, PC (57) ABSTRACT

The invention relates to any assay for the identification of nematicidal compounds such as anthelmintics for the control of nematodes. The assay comprises: (i) incubating a nematode sample (i.e. a "test nematode sample") containing a pre-determined amount of nematodes with an ingestable substrate labelled with a readily detectable label, under conditions suitable for nematode feeding, wherein said incubation is conducted in the presence of said candidate nematicidal compound or follows a pre-incubation of said nematode sample with said candidate nematicidal compound, and (ii) determining whether said candidate nematicidal compound affects nematode feeding by detecting an increase or decrease in ingested substrate as compared to that which has been ingested by a control nematode sample which has been incubated without said candidate nematicidal compound.

51 Claims, 4 Drawing Sheets

OTHER PUBLICATIONS

Haughland, R. Handbook of Fluorescent Probes and Research Chemicals 6th ed. (molecular Probes: Eugene, OR) 1996, p. 109-115.*

Bansemir et al. (J. Parasitology (1994) 80(1): 24-28 (abstract only).*

Webster's II New Reiverside University Dictionary (1994) (Houghton-Mifflin: Boston, MA) p. 1167.*

Bansemir et al. "The Food Resource of Adult *Heligmosomoides polygyrus* in the Small Intestines" J. Parasitology (1994) 80(1): 24-28 (full paper).*

Bottjer, K.P. and Bone, L.W. (1985), "*Trichostrongylus Colubriformis*: Effect of Anthelmintics on Ingestion and Oviposition," Int. J. Paraasit. 15(5): 501-503.

Geary, T.G. et al. (1993), "*Haemonochus contortus*: Invermectin-inducted Paralysis of the Pharynx," Exp. Parasit. 77:88-96.

Paiement, J-P et al. (Jul. 1999), *Haemonchus contortus*: Effects of Glutamate, Invermectin, and Moxidectin on Inulin Uptake Activity in Unselected and Invermectin-Selected Adults, Exp. Parasit. 92:193-198.

Brownlee, D.J.A. et al. (1997), "Actions of the anthelminitic invermectin on the pharyngeal muscle of the parasitic nematode, *Ascaris suum*," Parasitology 115:553-561.

Bird, A.F. and Ryder, M.H. (1993), "Feeding of the Nematode *Acrobeloides nanus* on Bacteria," J. Nematol. 25(3):493-499.

* cited by examiner

FEEDING ASSAY FOR IDENTIFYING NEMATICIDAL COMPOUNDS

FIELD OF THE INVENTION

This invention relates to the identification of nematicidal compounds such as anthelmintics for the control of nematodes. In particular, the invention relates to a feeding assay allowing for the high throughput identification and assessment of candidate nematicidal compounds.

BACKGROUND TO THE INVENTION

Many species of nematodes are parasites of considerable medical, veterinary and agricultural significance. For example, nematodes of the Orders *Strongylida, Strongyloides, Ascaradida, Oxyurida* and *Trichocephalida* include many species that cause disease in humans, sheep, cattle, pigs and other species. Further, nematodes of the Orders *Tylenchida* and *Aphelenchida*, and others, include species which are parasitic of important crop plants and fungi.

Due to resistance development (e.g. anthelmintic resistance) and concerns over safety of existing nematicide compounds (e.g. the widely used soil fumigant, methyl bromide, is known to damage the ozone layer; while the use of others is of concern due to their broad toxicity), there is an ongoing need for the identification of new anthelmintic compounds. Further, in the agricultural context, there is a need to identify DNA sequences that might be introduced into plants and fungi to confer nematode resistance.

One possible site of action for new useful nematicidal compounds and products of resistance genes is the muscular pharyngeal pump which is involved in nematode feeding and the maintenance of internal hydrostatic pressure for nematode structure and motility. The present invention proposes a feeding assay based upon the measurement of pharyngeal pumping, which allows for the high throughput identification and assessment of candidate compounds capable of promoting or inhibiting pharyngeal pumping.

DISCLOSURE OF THE INVENTION

In a first aspect, the present invention provides an assay for identifying and/or assessing candidate nematicidal compounds, said assay comprising the steps of;

(i) incubating a nematode sample (i.e. a "test nematode sample") containing a predetermined amount of nematodes with an ingestable substrate labelled with a readily detectable label, under conditions suitable for nematode feeding, wherein said incubation is conducted in the presence of said candidate nematicidal compound or follows a pre-incubation of said nematode sample with said candidate nematicidal compound, and (ii) determining whether said candidate nematicidal compound affects nematode feeding by detecting an increase or decrease in ingested substrate as compared to that which has been ingested by a control nematode sample which has been incubated without said candidate nematicidal compound.

The "control nematode sample" contains nematodes of the same species or strain as the test nematode sample, contains the same predetermined amount of nematodes as the test nematode sample and is incubated under substantially the same conditions and for substantially the same duration as the test nematode sample. The control nematode sample is also incubated with an amount of ingestable substrate which is equivalent to that used in the test nematode sample incubation. Where the incubation is conducted in suspension, some volumetric adjustment may be made (using water or phosphate buffered saline or M9 buffer; Brenner, S., The genetics of *Caenorhabditis elegans*. *Genetics*, Vol. 77, pp 71–94, 1974) to the control nematode sample to account for the omission of the candidate nematicidal compound.

The incubation may be conducted upon a solid media (e.g. agar), but is more preferably conducted in suspension (e.g. in M9 or phosphate buffered saline). The incubation may be carried out at any temperature suitable for nematode feeding. However, for the sake of convenience, the incubation is preferably conducted at room temperature (i.e. about 22° C.). The duration of the incubation may be of any length within which nematode feeding would normally be expected to occur. Preferred durations for the incubation are within the range of from about 0.25 to 5 hours or, more preferably, from about 0.5 to 2 hours, or, most preferably, are of about 1 hour.

The incubation may optionally be conducted with an amount of an agent known to stimulate nematode feeding (e.g. 80 µM to 5 mM serotonin with a concentration of approximately 2.5 mM offering optimal stimulation of pumping and a concentration of approximately 0.15 to 0.5 mM thereby offering optimal sensitivity to antagonists or inhibitors of pharyngeal pumping.

Where the assay involves a pre-incubation of the nematode sample with a candidate nematicidal compound, the pre-incubation may be conducted upon a solid media or in suspension. Preferably, the pre-incubation is carried out at room temperature. The duration of the pre-incubation is preferably in the range of from about 0.1 to 24 hours or, more preferably, from 0.5 to 2 hours. However, where the candidate nematicidal compound is selected from peptides, polypeptides, proteins and nucleic acids, the duration of the pre-incubation may be up to at least approximately the duration of one generation of the nematodes in the nematode sample. In the case of *C. elegans*, this would be approximately 3 days.

The predetermined amount of nematodes used in the test and control nematode samples may be of any suitable amount. Conveniently, the test and control nematode samples are prepared using an identical volume of a stock nematode suspension. In a preferred embodiment of the present invention, the incubation is conducted in a well of a 96-well plate. In that case, the preferred predetermined amount of nematodes used may be in the range of about 2.5% (v/v) to 15% (v/v) packed (1× the force of gravity) adult nematodes in the final assay volume, corresponding to between about 400 and about 2,600 adult nematodes in a 100 µl assay volume. More preferably the amount of nematodes is 10% (v/v) corresponding to about 1,700 adult nematodes in a 100 µL assay volume or about 8,500 adult nematodes in a 500 µL assay volume.

The ingestable substrate is labelled with a readily detectable label such as a radioisotope label or, more preferably, a fluorescent label. It is preferred that the ingestable substrate consists of discrete particles which are sized to allow them to be pumped by the pharyngeal pump. It is also preferred that the ingestable substrate is not immediately passed through the nematode gut following ingestion, but is retained in the gut for a period of time which is longer than the duration of the incubation. Most preferably, the ingestable substrate consists of microsphere beads, preferably made of an inert polymer such as polystyrene, polyvinyl or copolymers thereof, which have a mean diameter of less than about 5 µm, more preferably, between about 0.9 and 1.5 µm. Using microsphere beads with a mean diameter of less than about 0.25 µm, may also allow for the assay to be applied to nematodes which are stylet feeders.

The candidate nematicidal compound may be selected from inorganic compounds or organic compounds (including peptides, polypeptides, proteins and nucleic acids) or mixtures thereof. Peptides, polypeptides, proteins and nucleic acids may be presented to the test nematode sample on the surface of, or contained within, bacteria or other host cells.

To determine whether the candidate nematicidal compound affects nematode feeding, the amount of ingested substrate is detected and compared to that which has been ingested by the control nematode sample. This may entail firstly halting nematode feeding by, for example, removing the nematodes from the ingestable substrate or, more preferably, by immobilising or killing the nematodes (e.g. by adding sodium azide to 10–20 mM or by adding hot water), and then detecting the amount of substrate which has been ingested or, alternatively, remains following the incubation (i.e. the uningested residual).

Conveniently, the incubation is conducted in a mesh-bottomed vessel which allows for uningested substrate to be washed through and away from the nematodes. For example, a mesh-bottomed 96-well plate such as Millipore Multi-screen N20 plates (custom order no. SE3R090M6), which comprise a clear polystyrene type body with a nylon mesh welded on to form the base of the wells. The body and mesh are fitted into a thermoplastic underdrain forming a gasket for filtration. The nylon mesh used may have a pore size of 5 µm to 25 µm depending upon the diameter of the nematode species being tested and the mean diameter of the ingestible substrate particles. For *C. elegans*, a pore size of 11 µm to 20 µm may be used with 20 µm being preferred.

Alternatively, through the use of ingestable substrate which are magnetic microsphere beads, uningested substrate may be readily removed from the nematodes by magnetic separation methods.

A detected increase or decrease in feeding from the test nematode sample is indicative of a possible promotion or inhibition of pharyngeal pumping by the candidate nematicidal compound. As foreshadowed above, promotion or inhibition of pharyngeal pumping may be lethal to nematodes through starvation, unbalancing of hydrostatic pressure or by depleting the nematodes energy reserves.

The assay according to the present invention allows for the high throughput identification and assessment of candidate nematicidal compounds. As such, the assay may be applied to compounds belonging to natural product collections, compounds belonging to libraries of chemically synthesised compounds, compounds belonging to combinatorial libraries, and gene expression libraries (e.g. by feeding the nematodes with bacteria containing or expressing library genes in various formats such as single or double-stranded RNA, DNA or protein). The assay may also be applied to a combination of two or more compounds, to allow for the identification and/or assessment of synergistic "cocktails" of nematicidal compounds.

In a second aspect, the present invention provides an assay for identifying and/or assessing candidate nematicidal compounds, said assay comprising the steps of:

(i) incubating a nematode sample (i.e. a "test nematode sample") containing a predetermined amount of nematodes with an ingestable substrate labelled with a readily detectable label, under conditions suitable for nematode feeding, (ii) thereafter exposing the nematode sample in the presence of said candidate nematicidal compound, and (iii) determining whether said candidate nematicidal compound affects passage of the ingested substrate through the nematode gut.

The incubation of the nematode sample with an ingestable substrate may be conducted as described above in relation to the first aspect. The nature and predetermined amount of the ingestable substrate is also as described above.

The exposure of the nematode sample with the candidate nematicidal compound may be conducted in a manner similar to the pre-incubation described above in relation to the first aspect. In this case, however, the duration of the exposure is preferably in the range of 0.5 to 2 hours, more preferably, about 1 hour.

The candidate nematicidal compound for use in the method of the second aspect may be selected from inorganic compounds or organic compounds (including peptides, polypeptides, proteins and nucleic acids) or mixtures thereof. Peptides, polypeptides, proteins and nucleic acids may be presented to the test nematode sample on the surface of, or contained within, bacteria or other host cells.

The step of determining whether the candidate nematicidal compound affects passage of the ingested substrate may be determined by detecting an increase or decrease in the rate of passage of the ingested substrate through the nematode gut. This may be achieved by measuring the amount of ingested substrate that has either passed through the nematode gut or is retained in the gut, or both, at certain time intervals following incubation with the candidate nematicidal compound and comparing those amounts with equivalent measurements obtained from a control nematode sample (i.e. a sample which has not been exposed to the candidate nematicidal compound).

In a third aspect, the present invention provides a nematicidal compound identified by the assay of the first or second aspect.

The terms "comprise", "comprises" and "comprising" as used throughout the specification are intended to refer to the inclusion of a stated step, component or feature or group of steps, components or features with or without the inclusion of a further step, component or feature or group of steps, components or features.

The invention is hereinafter further described with reference to the following non-limiting example and accompanying figures.

BRIEF DESCRIPTION OF THE ACCOMPANYING FIGURES

FIG. 1 shows the effect of 5 mM serotonin and incubation time on pharyngeal pumping of fluorescent microsphere beads by *C. elegans*. Fluorescence microscopy fields show aliquots taken from two wells of a 24-well plate containing *C. elegans* from the same population. The nematodes in each well were incubated with fluorescent microsphere beads for up to three hours. The incubation, magnification, exposure and scanning conditions were equivalent in all cases except that the nematodes shown in the upper five panels received no serotonin whilst the nematodes in the lower series of five panels received 5 mM serotonin. Incubation conditions were 10% (v/v) nematodes and 0.1% (w/v) beads in M9 buffer. The magnification is approximately 40–50×. At the times indicated, duplicate aliquots were removed from the wells of the 24-well plate to the wells of a mesh-bottomed 96-well plate, further activity was stopped by addition of sodium azide to 10 mM. At the completion of the experiment, uningested beads were washed away and the samples were viewed under the fluorescence microscope. The fluorescent intensity of the aliquots was also measured in the fluorimeter as shown in FIG. 2. In other experiments performed under similar conditions, high magnification examination showed that approximately 80% of the treated nematodes had ingested one or more microsphere beads. Strongly labelled nematodes were estimated to contain at least several hundred microsphere beads.

FIG. 2 shows fluorimetry of the samples illustrated in FIG. 1. Aliquots of the samples shown in FIG. 1 were read with a gain of 30 on a BMG PolarStar Plate Fluorimeter. The 180 minute time point was not read because there were insufficient nematodes left for full aliquots. Points with error bars represent the means±standard deviations of duplicate wells of the 96-well plate (not duplicate experiments) containing approximately 1700 nematodes each.

FIG. 3 provides log-dose response curves for the effect of serotonin on the rate of pharyngeal pumping, and therefore of bead ingestion. In separate experiments (not shown) it has been confirmed by videotaping nematodes under Nomarski interference microscopy that serotonin at these doses directly affects pharyngeal pumping rate in a manner consistent with the data presented here. The assay was performed in the wells of a 24-well plate using M9 buffer, 0.1% fluorescent beads and 10% (v/v) nematodes. Incubation was for 60 minutes at room temperature. At the end of the assay period, aliquots of the nematodes were transferred to the wells of a mesh-bottomed plate and prepared for fluorimetry as described in the above description of FIG. 2. A gain of 30 provides the most sensitivity at low doses of serotonin, but at higher doses the signal in the fluorimeter saturates (flat top to the blue curve). Therefore the plate containing the nematodes was read with three different gain settings to allow extraction of maximum information for both high and low concentrations of serotonin. Note that high concentrations of serotonin (5 mM) are suboptimal, with 2.5 mM serotonin providing the strongest relative signal. Points with error bars represent the means±standard deviations of duplicate wells of the 96-well plate (not duplicate experiments) containing approximately 1700 nematodes each.

FIG. 4 shows the effects of varying the percentages of nematodes and fluorescent microbeads on the signal intensity. This assay was performed in duplicate in the wells of a 96-well plate. The assay was performed in the presence of 2.5 mM serotonin in M9 buffer for 60 minutes at room temperature. Gain setting was 30. Points with error bars represent the means ±standard deviations of independent duplicate wells of the 96-well plate containing approximately 1700 nematodes each.

Panel 4a shows the results obtained when the whole assay was performed and read in the 96-well mesh-bottomed plate.

Panel 4b shows the result when the samples from 4a were transferred from the mesh-bottomed plate to a standard clear polystyrene microplate for fluorimetry.

Figure 1:
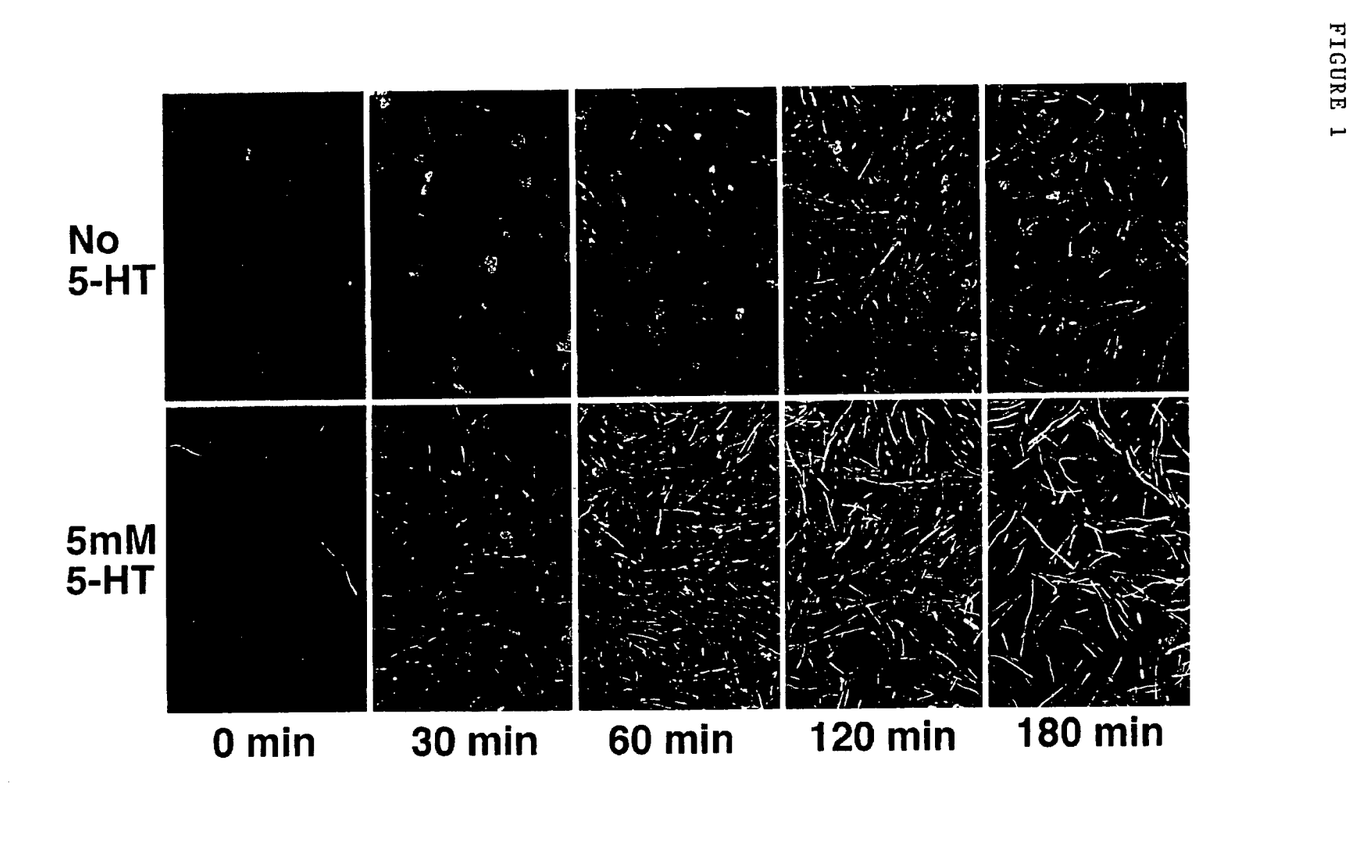
Figure 2:
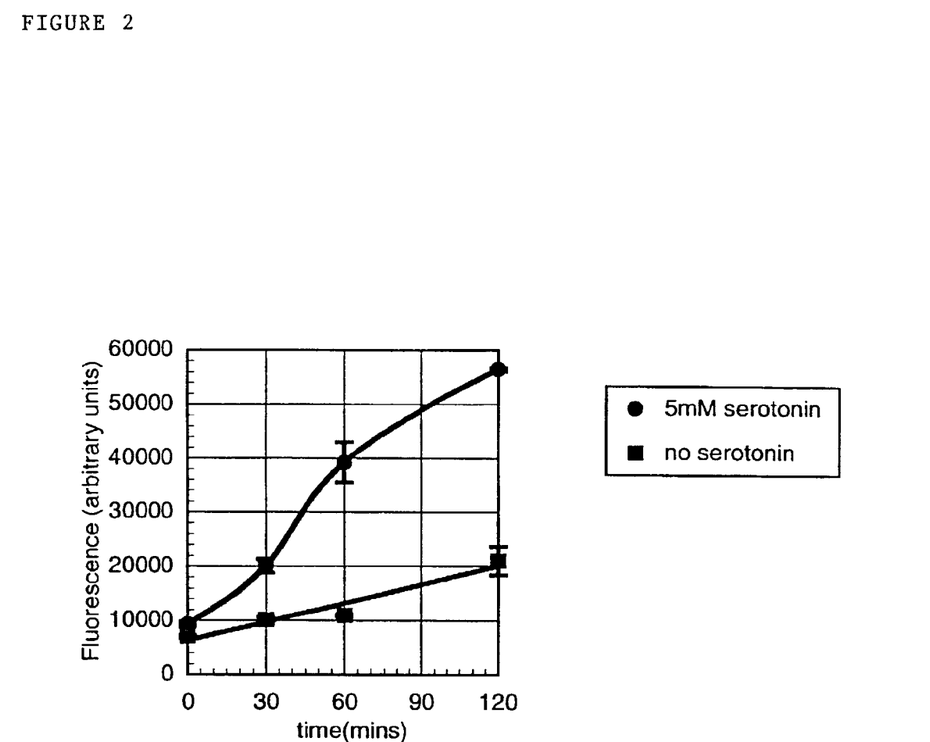
Figure 3:
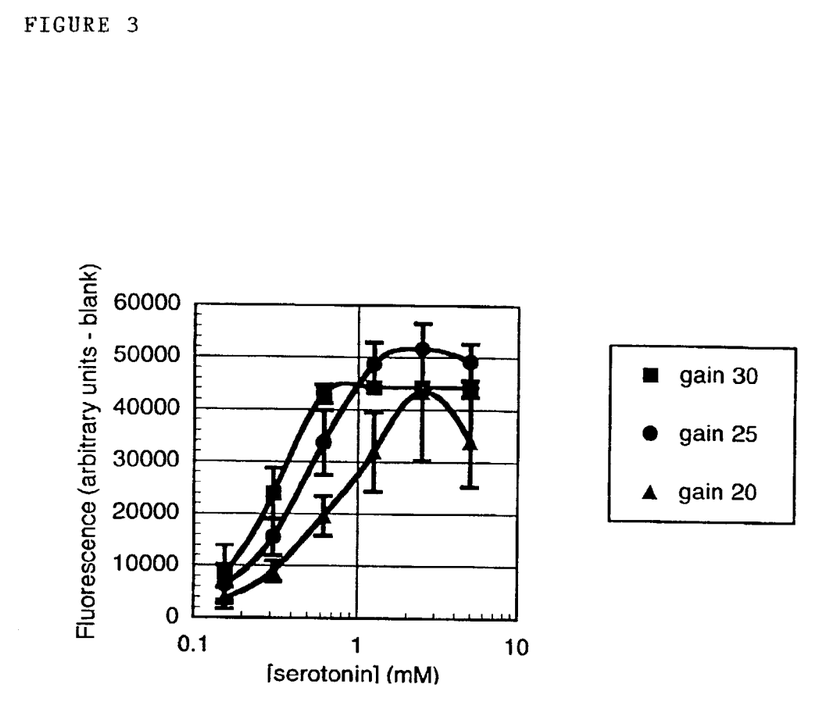
Figure 4:
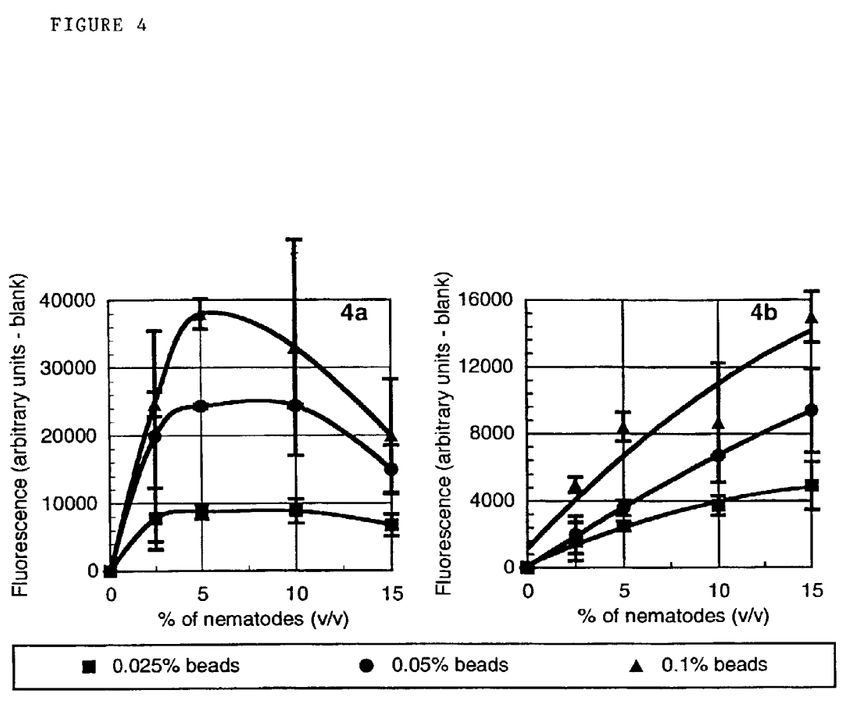

Note that when read in the mesh-bottomed plate (4a), although the absolute signal strength is high, there is a significant depression of signal at higher concentrations of nematodes. Also very high percentage variations were observed. In this situation the highest signal strength obtained was with 5% (v/v) nematodes and 0.1% (w/v) microbeads. When the same samples of nematodes were transferred to a standard clear 96-well plate for fluorimetry (4b) the signal was lower but it continued to increase with concentrations of nematodes up to 15% and percentage variation between duplicate wells was generally lower. This difference is attributed to some form of self absorption or scattering of the exciting and/or emitted wavelengths at high nematode densities in the mesh-bottomed plate. Why this phenomenon should be more severe in the mesh-bottomed plate is unclear, although it has been observed that the background fluorescence and general reflectivity of these plates is higher than for conventional clear 96-well plates.

EXAMPLE

Methods and Materials

1. *C. elegans* of the Bristol N2 strain (Brenner, S. 1974. *The genetics of Caenorhabditis elegans. Genetics* 77: 71–94) were cultured at room temperature on HMS174 *E. coli* bacteria (Campbell, J. L., Richardson, C., and Studier, F. W. 1978. *Genetic recombination and complementation between bacteriophage T7 and cloned fragments of T7 DNA.* Proc. Natl. Acad. Sci. USA. 75: 2276–2280) spread on a 150 mm diameter petri dish containing enhanced NGM 3% (w/v) (Avery, L., and Horvitz, H. R. 1990. *Effects of starvation and neuroactive drugs on feeding in Caenorhabditis elegans.* J. Exp. Zool. 253: 263–270) agar until a good population of adult nematodes was present, but food reserves had not been exhausted. (Nematodes may be mass cultured in suspension if required).

2. The nematodes were collected by washing with 10 mL and then 5 mL of M9 buffer and filtering over a 20 μm nylon mesh (Nytal—Catalogue no. BCNY-HD002-20) to retain adult nematodes.

3. Adult nematodes were collected from the mesh using a pasteur pipette and allowed to settle in an eppendorf tube at 1 g for 10 minutes. This packed volume was used to calculate quantities of nematodes for experiments and assays, although nematodes were resuspended in 2–10 volumes of M9 buffer for transfer. Quantitative transfers of nematodes were performed using a Gilson Pipetman P200 or equivalent and a yellow tip with 5 mm cut off the sharp end.

4. 96-well mesh-bottomed plates were blocked prior to performing the assay in order to minimise non-specific adherence of fluorescent microsphere beads. To block, 200 μL of a 0.1% (w/v) suspension of dark blue-dyed, non-fluorescent microsphere beads with a mean diameter of 0.95 μm and a hydrophilic surface coating (Catalogue code DC03B, carboxylate-modified polystyrene/polyvinyl copolymer) (manufactured and supplied by Bangs Laboratories, Inc. 9025 Technology Drive. Fishers, Ind. 46038-2886, USA) were added to the plate and incubated overnight at room temperature with orbital shaking at 70 r.p.m. Prior to the assay, the bead suspension was removed under vacuum using a Millipore Multiscreen manifold. The plate was washed three times by pipetting 200 μL of M9 buffer into each well, allowing the plate to sit for 5 minutes and then sucking off the suspension.

5. The assay was either set up in the wells of a solid-bottomed 24-well plate using a final assay volume in the range of 0.5 to 1.0 mL or it was set up in the wells of a 96-well mesh bottomed plate (Millipore Multiscreen N20 plates, custom order no. SE3R090M6). In the latter case, the final assay volume was always 100 μL. The assay buffer in all cases was M9. The added volume of a stock of M9 and the added volume of double-distilled water were adjusted so as to achieve a final concentration of 1×M9 in the desired assay volume. A sufficient volume of a suspension of nematodes was added to the assay wells to give a final percentage in the range of 2.5% to 15% (v/v) depending on the experiment. A stock solution of the drug or test compound (e.g. serotonin) was added to the wells of the plate to give the desired final concentration. A sufficient volume of a suspension of fluorescent microsphere beads in double-distilled water was added to give a final concentration in the range of 0.025% to 0.1% (w/v) depending on the experiment.

6. The fluorescent beads were 1.30 µm uniformly dyed microsphere beads with a hydrophilic surface-coating. The fluorescence excitation maximum was 420 nm and the emission maximum was 485 nm (catalogue code FC04F, carboxylate-modified polystyrene/polyvinyl copolymer, manufactured and supplied by Bangs Laboratories, Inc. 9025 Technology Drive, Fishers, Ind. 46038-2886, USA).

7. The assay plate was placed on an orbital shaker at 70 r.p.m. at room temperature and incubated for up to 180 minutes (normally 60 minutes), under subdued illumination.

8. At the end of the incubation 20 µL of 100 mM sodium azide was added to the wells of the 96-well mesh plate. When the incubation had been conducted in 24-well plates, 100 µL aliquots were removed to the wells of a 96-well mesh-plates and then the sodium azide was added to these aliquots. The nematodes were left in the sodium azide for 20 minutes before being washed.

9. Washing comprised five washes with 200 µL each time of 1%(w/v) sodium lauryl sulphate (Sigma) in M9 buffer. The first two washes involved pipetting the solution up and down in the wells of the plate ten times each wash. These washes were followed by five washes with M9 buffer only. At the end of each washing step solutions were removed by sucking through the mesh using a Millipore Multiscreen vacuum manifold.

10. 50 µL M9 was added to the wells of the mesh plate and it was placed on a piece of black cardboard before being read in the PolarStar fluorimeter with excitation at 420 nm and emission at 485 nm. Various gain settings (usually 20, 25 or 30) were used in order to maximise the dynamic range of the assay.

11. In some cases the nematodes were subsequently pipetted out of the mesh plate into a standard clear or black solid plastic 96-well plate. The wells of the mesh plate were rinsed out with a further 100 µL of M9 buffer which was transferred to the corresponding wells of the clear or black 96-well plate. This latter plate was then read in the fluorimeter at a similiar or higher gain setting.

12. It was generally found that nematodes which had access to ample food supplies in the 24 hours prior to the assay gave the best results. The quality of the results was assessed according to the following ratio. Signal strength due to nematodes incubated with beads in the presence of 2.5 mM serotonin for 60 minutes divided by the signal strength due to nematodes incubated with beads for 60 minutes without serotonin. It is considered that a ratio of over 3 to be acceptable in that it gives a sufficient dynamic range in the assay to detect agonists and antagonists reliably, and a preferable ratio to be greater than 4 and, most preferably, greater than 6.

RESULTS

Experiments show that the detection limit for the fluorimeter when set at a gain of 30 is between 1,000 and 10,000 beads, i.e. approximately 100 nematodes ingesting between 10 and 100 microsphere beads each.

100 µL packed volume of adult nematodes contains approximately 16–18,000 nematodes.

In one experiment, 10 µL packed volume of adult nematodes containing 1,600–1,800 nematodes, gave a signal of 6246 (arbitrary fluorescence intensity units at a gain setting of 30) over control after a two hour incubation. Therefore each serotonin-treated nematode ingested on average 417 microsphere beads more than a control nematode. However, in later experiments, when conditions had been optimised, a signal strength over control was obtained from the same volume of nematodes that was approximately 6 times greater indicating that the average number of microsphere beads ingested by nematodes under these conditions could be up to approximately 2,400 more than a control nematode.

DISCUSSION

The example shows the feasibility of the assay according to the present invention, by demonstrating the ready detection of increased microsphere bead ingestion when serotonin is present during the incubation.

The observation that the nematodes ingest several hundred microsphere beads (and that these initially tend to aggregate in clumps immediately posterior to the pharynx and are subsequently found throughout the entire postpharyngeal alimentary canal), suggests that the sensitivity of the assay (when using fluorescent-labelled microsphere beads) may be enhanced by utilising a tissue solubiliser to digest the nematodes prior to fluorimetry. However, experiments using alkaline hypochlorite to solubilise nematodes resulted in a decrease rather than an increase in signal strength.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An assay for identifying and/or assessing candidate nematicidal compounds, said assay comprising the steps of:
   (i) incubating a nematode sample containing a predetermined amount of nematodes with an ingestable substrate labelled with a readily detectable label, under conditions suitable for nematode feeding, wherein said incubation is conducted in the presence of said candidate nematicidal compound or follows a pre-incubation of said nematode sample with said candidate nematicidal compound, and
   (ii) determining whether said candidate nematicidal compound affects nematode feeding by detecting an increase or decrease in ingested substrate as compared to that which has been ingested by a control nematode sample which has been incubated without said candidate nematicidal compound, and wherein the ingestable substrate consists of microsphere beads.

2. An assay according to claim 1, wherein the step of incubating the nematode sample is conducted in suspension.

3. An assay according to claim 1, wherein the step of incubating the nematode sample is conducted at room temperature.

4. An assay according to claim 1, wherein the duration of the incubation is within the range of 0.25 to 5 hours.

5. An assay according to claim 4, wherein the duration of the incubation is within the range of 0.5 to 2 hours.

6. An assay according to claim 5, wherein the duration of the incubation is 1 hour.

7. An assay according to claim 1, wherein the incubation is conducted in the further presence of an amount of an agent which stimulates nematode feeding.

8. An assay according to claim 7, wherein said agent is serotonin.

9. An assay according to claim 8, wherein said serotonin is present at a concentration in the range of 80 µM to 5 mM.

10. An assay according to claim 1, wherein said assay coprises a pre-incubation of the nematode sample with a candidate nematicidal compound.

11. An assay according to claim 10, wherein said pre-incubation is conducted in suspension.

12. An assay according to claim 10, wherein said pre-incubation is conducted at room temperature.

13. An assay according to claim 12, wherein the duration of the pre-incubation is within the range of 0.1 to 24 hours.

14. An assay according to claim 13, wherein the duration of the pre-incubation is within the range of 0.5 to 2 hours.

15. An assay according to claim 1, wherein the microsphere beads are made of an inert polymer.

16. An assay according to claim 1, wherein the microsphere beads have a mean diameter of less than 5 µm.

17. An assay according to claim 16, wherein the microsphere beads have a mean diameter of between 0.9 and 1.5 µm.

18. An assay according to claim 17, wherein the microsphere beads have a mean diameter of less than 0.25 µm.

19. An assay according to claim 1, wherein the candidate nematicidal compounds are inorganic compounds.

20. An assay according to claim 1, wherein the candidate nematicidal compounds are organic compounds.

21. An assay according to claim 20, wherein the candidate nematicidal compounds are peptides, polypeptides, proteins and nucleic acids.

22. An assay according to claim 1, wherein the ingestable substrate is labelled with a radioisotope label or fluorescent label.

23. An assay according to claim 1, wherein the ingestable substrate is labelled with a fluorescent label and the step of determining whether said candidate nematicidal compound affects nematode feeding by detecting an increase or decrease in ingested substrate is achieved with fluorimetry.

24. An assay according to claim 23, wherein the nematodes of said nematode sample are solubilised prior to fluorimetry.

25. An assay according to claim 1, wherein the nematodes in the nematode sample are of a species belonging to the order of *Strongylida, Strongyloides, Ascaradida, Oxyurida, Trichocephalida, Tylenchida* or *Aphelenchida*.

26. An assay according to claim 1, wherein the nematodes in the nematode sample are of a species of rhabditid nematodes.

27. An assay according to claim 1, wherein the nematodes in the nematode sample are of a species belonging to the genus *Caenorhabditis*.

28. An assay according to claim 1, wherein the nematode in the nematode sample is *Caenorhabditis elegans*.

29. An assay for identifying and/or assessing candidate nematicidal compounds, said assay comprising the steps of:
(i) incubating a nematode sample containing a predetermined amount of nematodes with an ingestable substrate labelled with a readily detectable label, under conditions suitable for nematode feeding
(ii) thereafter exposing the nematode sample in the presence of said candidate nematicidal compound, and
(iii) determining whether said candidate nematicidal compound affects passage of the ingested substrate through the nematode gut,
and wherein the ingestable substrate consists of microsphere beads.

30. An assay according to claim 29, wherein the step of incubating the nematode sample is conducted in suspension.

31. An assay according to claim 29, wherein the step of incubating the nematode sample is conducted at room temperature.

32. An assay according to claim 29, wherein the duration of the incubation is within the range of 0.25 to 5 hours.

33. An assay according to claim 32, wherein the duration of the incubation is within the range of 0.5 to 2 hours.

34. An assay according to claim 33, wherein the duration of the incubation is 1 hour.

35. An assay according to claim 29, wherein the incubation is conducted in the further presence of an amount of an agent which stimulates nematode feeding.

36. An assay according to claim 35, wherein said agent is serotonin.

37. An assay according to claim 36, wherein said serotonin is present at a concentration in the range of 80 µM to 5 mM.

38. An assay according to claim 37, wherein said step of exposing the nematode sample to the candidate nematicidal compound is conducted in suspension.

39. An assay according to claim 37, wherein said exposing step is conducted at room temperature.

40. An assay according to claim 39, wherein the duration of the exposing step is within the range of 0.5 to 2 hours.

41. An assay according to claim 40, wherein the duration of the exposing step is 1 hour.

42. An assay according to claim 29, wherein the microsphere beads are made of an inert polymer.

43. An assay according to claim 29, wherein the microsphere beads have a mean diameter of less than 5 µm.

44. An assay according to claim 43, wherein the microsphere beads have a mean diameter of between 0.9 and 1.5 µm.

45. An assay according to claim 44, wherein the microsphere beads have a mean diameter of less than 0.25 µm.

46. An assay according to claim 29, wherein the candidate nematicidal compounds are inorganic compounds.

47. An assay according to claim 29, wherein the candidate nematicidal compounds are organic compounds.

48. An assay according to claim 47, wherein the candidate nematicidal compounds are peptides, polypeptides, proteins and nucleic acids.

49. An assay according to claim 29, wherein the ingestable substrate is labelled with a radioisotope label or fluorescent label.

50. An assay according to claim 29, wherein the ingestable substrate is labelled with a fluorescent label and the step of determining whether said candidate nematicidal compound affects passage of the ingested substrate through the nematode gut is achieved with fluorimetry.

51. An assay according to claim 50 wherein the nematodes of said nematode sample are solubilised prior to fluorimetry.

* * * * *